(12) United States Patent
Milo et al.

(10) Patent No.: US 7,842,123 B2
(45) Date of Patent: Nov. 30, 2010

(54) EXTRACTION OF GAS FROM INFUSED LIQUID

(76) Inventors: Ehud Milo, 6a Noga Street, Haifa (IL) 34407; Simcha Milo, 6a Noga Street, Haifa (IL) 34407

( * ) Notice: Subject to any disclaimer, the term of this patent is extended or adjusted under 35 U.S.C. 154(b) by 0 days.

(21) Appl. No.: 12/429,106

(22) Filed: Apr. 23, 2009

(65) Prior Publication Data
US 2009/0199708 A1 Aug. 13, 2009

Related U.S. Application Data

(63) Continuation of application No. PCT/IB2007/002673, filed on Sep. 14, 2007.

(60) Provisional application No. 60/863,757, filed on Oct. 31, 2006.

(51) Int. Cl.
*B01D 19/00* (2006.01)

(52) U.S. Cl. .............................. 95/30; 95/261; 96/195; 96/196; 96/175

(58) Field of Classification Search .................. 95/261, 95/30; 96/195, 196, 175
See application file for complete search history.

(56) References Cited

U.S. PATENT DOCUMENTS

| | | | |
|---|---|---|---|
| 4,289,244 A | 9/1981 | Frankhouser et al. | |
| 4,900,308 A | 2/1990 | Verkaart | |
| 5,823,986 A | 10/1998 | Peterson | |
| 5,823,987 A | 10/1998 | Elgas et al. | |
| 5,824,212 A | 10/1998 | Brockhoff | |
| 5,997,516 A | 12/1999 | Caro et al. | |
| 6,019,824 A | 2/2000 | Schnell | |
| 6,053,967 A | 4/2000 | Heilmann et al. | |
| 6,264,601 B1 | 7/2001 | Jassawalla et al. | |
| 6,368,075 B1 | 4/2002 | Fremercy | |
| 6,689,315 B2 | 2/2004 | Linker et al. | |
| 6,730,267 B2 | 5/2004 | Stringer et al. | |
| 6,769,871 B2 | 8/2004 | Yamazaki | |
| 6,773,670 B2 | 8/2004 | Stringer et al. | |
| 6,827,862 B1 | 12/2004 | Brockhoff et al. | |
| 6,953,438 B2 * | 10/2005 | Milo | 601/2 |
| 6,960,322 B2 | 11/2005 | Stringer et al. | |
| 7,108,785 B1 | 9/2006 | Plechinger et al. | |
| 7,517,387 B2 * | 4/2009 | Chevallet et al. | 95/24 |

(Continued)

FOREIGN PATENT DOCUMENTS

CA 2311977 12/2000

(Continued)

*Primary Examiner*—Duane Smith
*Assistant Examiner*—Douglas J Theisen
(74) *Attorney, Agent, or Firm*—Fitch, Even, Tabin & Flannery

(57) ABSTRACT

Apparatus (20) for removing gas bubbles from a liquid to be infused to a patient wherein a gas trap (42) is located at the upper end of a vertical column (38, 40, 40*a*) having a lower inlet (44) and an upper outlet (56). A bracket (39) supports the column above the patient, and a bubble-separator (46, 39*a*, 47, 66, 63), positioned between the inlet and the outlet, causes gas bubbles to move toward the column axis as they rise so that they are captured in the gas trap (42). Liquid to be de-gasified is supplied from a vertical level above the column outlet and is delivered through the side outlet (56) to the patient below.

14 Claims, 5 Drawing Sheets

U.S. PATENT DOCUMENTS

| | | |
|---|---|---|
| 2005/0192525 A1* | 9/2005 | Wieting et al. ............ 604/6.09 |
| 2006/0008380 A1 | 1/2006 | Moozyckine et al. |
| 2006/0084836 A1 | 4/2006 | Hubbard et al. |

FOREIGN PATENT DOCUMENTS

| | | |
|---|---|---|
| DE | 195 23 718 | 1/1997 |
| EP | 1 066 851 | 1/2001 |
| GB | 1 352 166 | 5/1974 |
| JP | 49 15341 | 4/1974 |
| WO | WO 92/04060 | 3/1992 |
| WO | WO 01/41655 | 6/2001 |

\* cited by examiner

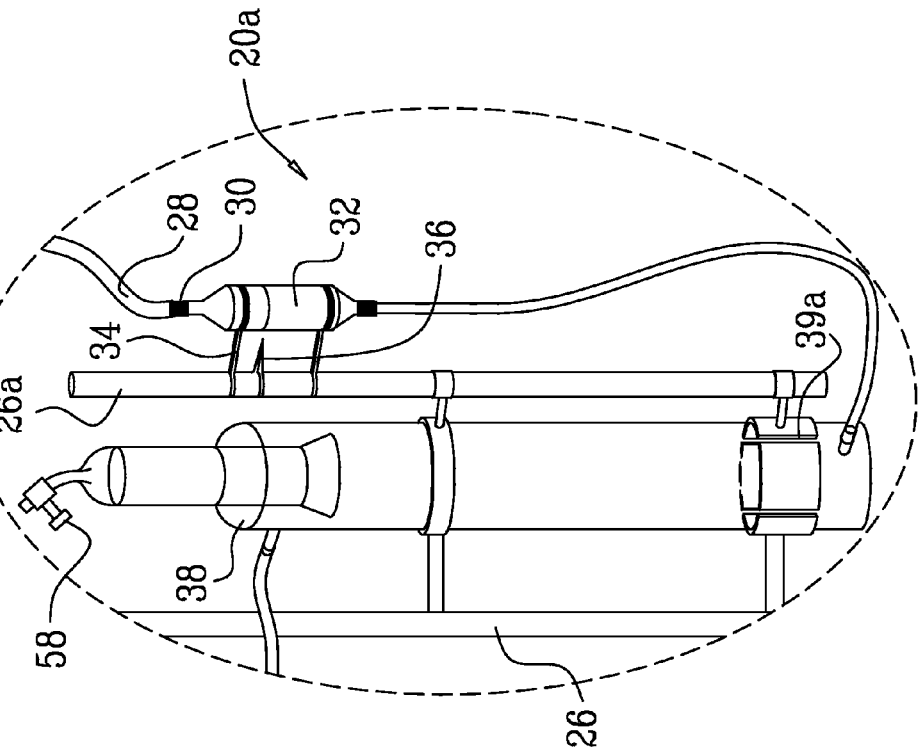
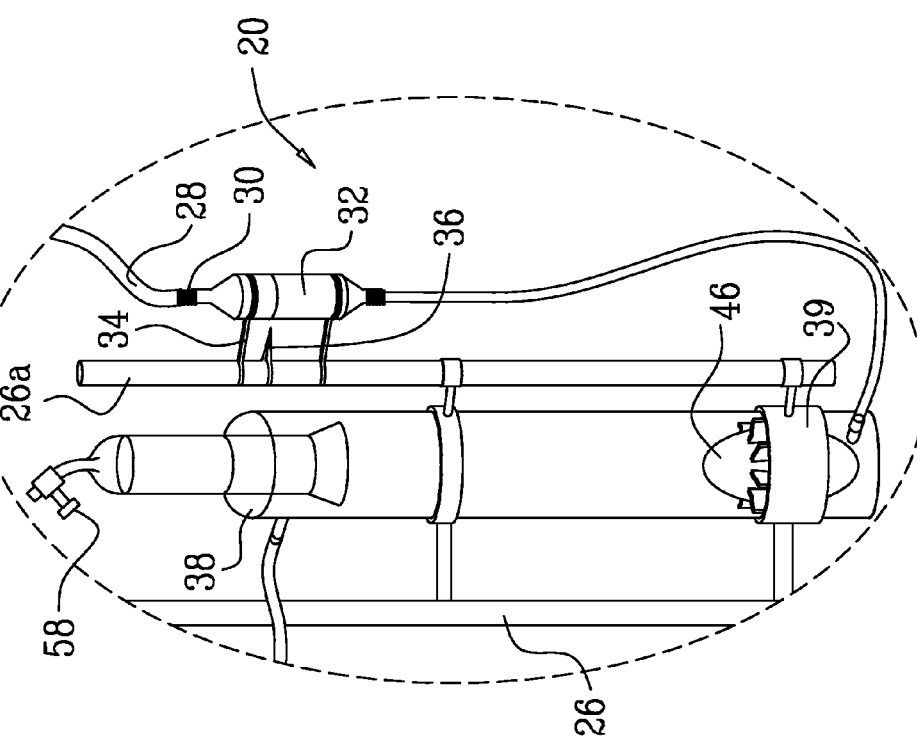

EXTRACTION OF GAS FROM INFUSED LIQUID

CROSS-REFERENCE TO RELATED APPLICATION

This application is a continuation of International Application No. PCT/IB2007/002673, filed Sep. 14, 2007, which claims the benefit of U.S. Provisional Patent Application 60/863,757, filed Oct. 31, 2006, the disclosures of both of which are incorporated herein by reference.

FIELD OF THE INVENTION

The present invention relates generally to medical devices, and specifically to methods and devices for removing gas bubbles from a stream of fluid being infused into a patient.

BACKGROUND OF THE INVENTION

The introduction of air into the vascular system is a potential complication of many procedures involving infusion of blood or other fluids. Air bubbles entrained in the infused fluid can cause air emboli, with potentially fatal consequences. In patients who undergo repeated infusion in large volumes, such as kidney failure patients being treated by hemodialysis, even small concentrations of air in the infused fluid can have serious cumulative effects. Although modern dialysis machines generally include a bubble trap, small bubbles may still penetrate therethrough into the blood being re-infused.

Various methods and devices are known in the art for eliminating air bubbles from blood. For example, PCT International Publication WO 01/41655, whose disclosure is incorporated herein by reference, describes a device that uses ultrasonic energy to cause microbubbles in a stream of liquid to be concentrated in a particular area of the flow (such as the center or one side of a tube carrying the liquid flow). A downstream vent tube then removes these bubbles into a sidestream, which is directed to a filter.

As another example, U.S. patent Application Publication US 2005/0192525, the disclosure of which is incorporated herein by reference, describes a system for removing gas bubbles from blood during circulatory assist procedures. In an active filter, the bubbles are forced to the center of a disposable filter chamber and are thereby removed from the blood before it reaches a peripheral exit from the filter. Inside the filter, a rotatable impeller with a magnetic coupler is driven by an external magnetic driver, spinning the blood and thus causing the lower density bubbles to move toward the central of the blood filter by centripetal force. The bubbles collect in a gas trap, from which the gas is bled off through a bleed valve. Other systems for removing gas from blood using a magnetically-driven impeller are described in U.S. Pat. Nos. 6,730,267, 6,773,670 and 6,960,322, whose disclosures are also incorporated herein by reference.

Other devices for removing gas bubbles from flowing blood have used a cyclone device, without moving parts, to cause the blood to flow in a helical path. Such devices are described, for example, in U.S. Pat. Nos. 5,824,212 and 6,053,967, whose disclosures are incorporated herein by reference. The rotating cyclone stream causes the air to be forced into the radial center of the stream, where it may be separated from the liquid.

SUMMARY OF THE INVENTION

Embodiments of the present invention provide improved methods and devices for removing gas bubbles from blood or other liquid to be infused to a patient. In some of these embodiments, the liquid is caused to flow upward through a column wherein the bubbles are caused to migrate to the central axis of the column where they are removed by vacuum at the upper end of a gas trap while the liquid, devoid of bubbles, flows out of the column and into the patient's body. Slow gravity flow upward through the column is achieved by feed from an upper location and facilitates construction of the integral column-gas trap as a straightforward disposable component.

In one particular aspect, the invention provides apparatus for removing gas bubbles from a liquid to be infused to a patient, which apparatus comprises a vertically oriented column, having a longitudinal axis, a lower inlet for receiving the liquid, an upper outlet for exit of the liquid from the column, and a gas trap at the upper end thereof; bracket means which supports the column in an operative position at a vertical level above the patient; a bubble-separator positioned between said inlet and said outlet which causes gas bubbles to move toward the column axis as they rise in the liquid in said column so that they are captured in the gas trap which has an entrance aligned with the column axis; means for supplying liquid to be de-gasified from a vertical level above that of said column outlet, and means for delivering liquid exiting said side outlet to a lower location.

In another particular aspect, the invention provides apparatus for removing bubbles from a liquid to be infused to a patient, the apparatus comprising a vertical column, having a lower end and an upper end, and having an inlet adjacent the lower end for receiving liquid, a side outlet vertically thereabove for exit of the liquid from the column, and a gas trap adjacent the upper end; a bubble-separator which causes bubbles in the liquid in the column to move toward a central axis of the column as the liquid travels from the inlet to the outlet so as to enter the gas trap; and means for creating a vacuum in an upper region of the gas trap.

In a further particular aspect, the invention provides A method for removing bubbles from a liquid for infusion to a patient, which method comprises supplying the liquid which contains bubbles by gravity flow so as to enter a vertically oriented column through an inlet adjacent to a lower end thereof, which column has a central axis extending along its length and a gas trap located axially thereof and adjacent to its upper end, and to exit from the column via a side outlet located vertically higher than the inlet; positioning the column at a location vertically higher than the patient and holding the column in an operative position during flow of the liquid through the column; actuating a bubble-separator which is located between the inlet to the column and the side exit which imparts energy to the liquid and bubbles in the column so as to cause bubbles to move toward the central axis where they rise and are captured in the gas trap as the liquid exits from the side outlet, and directing the liquid, with gas bubbles removed, from the side outlet to a lower location to effect gravity flow of liquid through the column.

The present invention will be more fully understood from the following detailed description of the embodiments thereof, taken together with the drawings in which:

BRIEF DESCRIPTION OF THE DRAWINGS

FIG. 1A is an enlarged perspective fragmentary view of the portion of the apparatus shown in FIG. 1 as depicted by the broken line encirclement;

FIG. 1B is an enlarged fragmentary perspective view of the portion of an apparatus as generally shown in FIG. 1 depicting an alternative embodiment of the portion of the broken line encirclement;

DETAILED DESCRIPTION OF EMBODIMENTS

Figure 1:
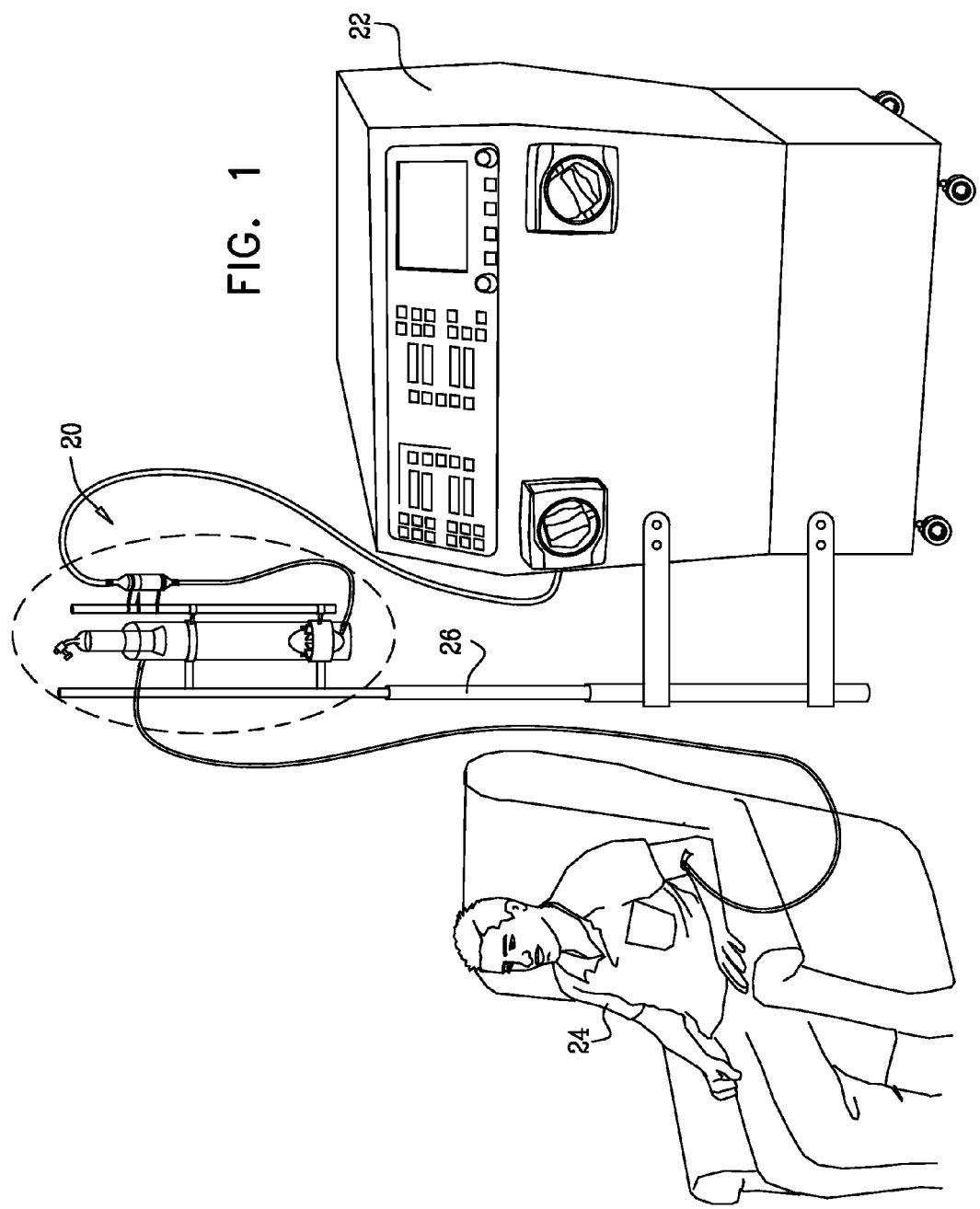
FIG. 1 is a schematic, pictorial illustration of apparatus for removal of gas from blood to be infused in use in conjunction with a dialysis machine, which embodies various features of the present invention.

FIG. 1 is a schematic, pictorial illustration showing a device 20 for removal of gas from liquid that is being infused; it is illustrated for use in conjunction with a dialysis machine 22 but is not limited to such use although it may have particular value there. The device 20 is constructed in accordance with one embodiment of the invention and is used to trap and remove small bubbles of gas that may have been entrained in the dialysis circuit, before the blood is returned to a patient 24. It should be understood that blood would, of course, be simultaneously removed from the arm of the patient 24 through a second line (not shown) which leads to the hemodialyzer. In contrast to extracorporeal circulation pumps that are used during cardiac surgery, for example, dialysis procedure is characterized by low blood flow rates (typically no more than about 450 cc/min) and low pressure. Although device 20 is expected to find particular application in dialysis, the principles of this device may similarly be applied in other clinical settings in which blood or other liquids are infused into a patient's vascular system. In contrast to most air filters and traps that are known in this art and are designed for high flow rates and fairly high pressures, the device 20 is particularly well-suited for low-pressure, low-flow applications, such as dialysis, although such need not be used exclusively and would be valuable for hemofiltration and other such procedures.

Figures 2, 2A:
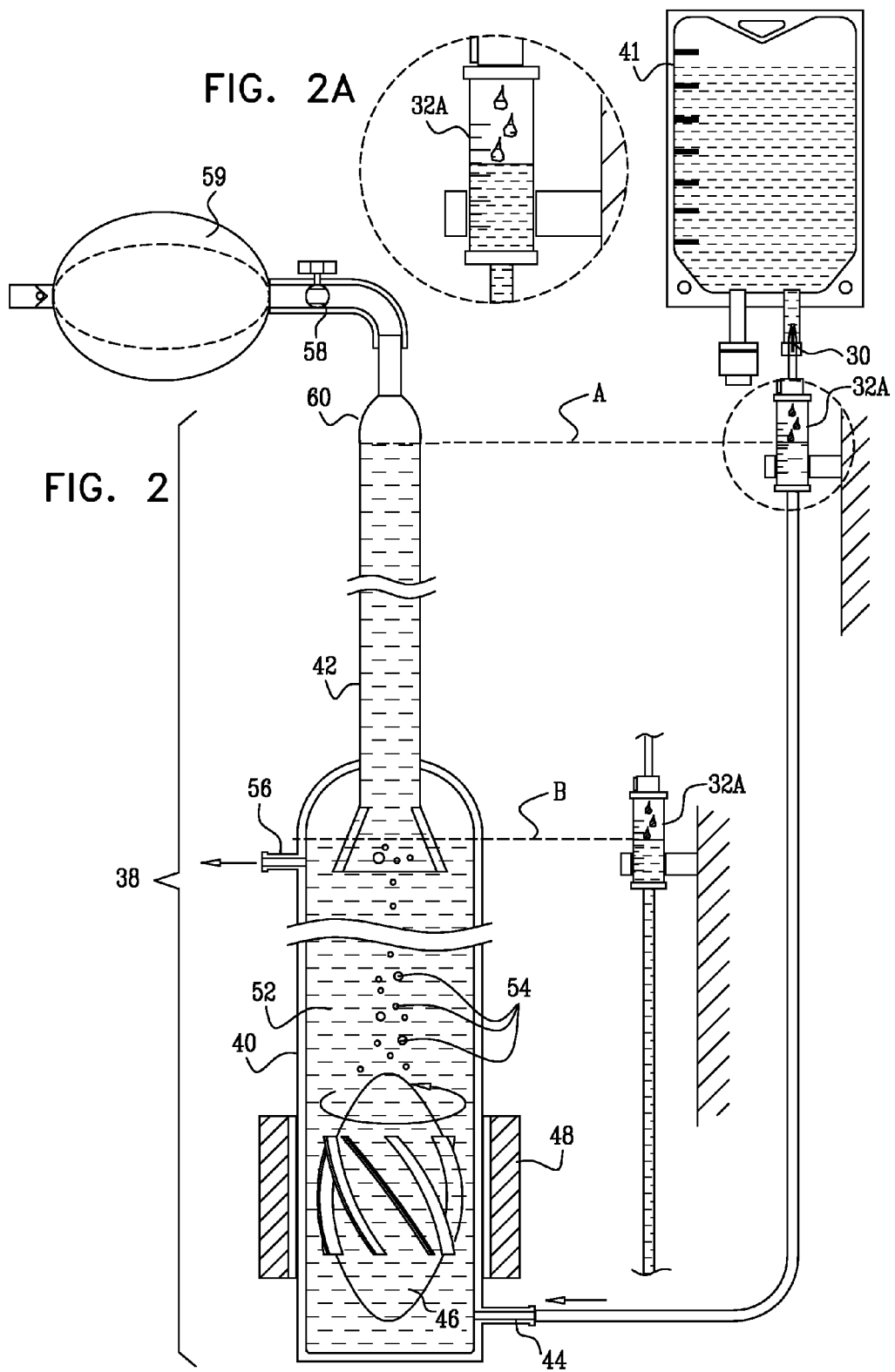
FIG. 2 is a schematic view shown mainly in cross of another embodiment of an apparatus for removal of gas from liquid to be infused.
FIG. 2A is an enlarged fragmentary view of the portion of the apparatus shown in FIG. 2 as depicted by the broken line encirclement.

The device 20, as best seen in FIGS. 1A and 2, comprises a separation column 38, which is conveniently supported in a vertical orientation on a fixture that includes a pole 26 which may be mounted on the dialysis machine 22. The column 38 contains an impeller 46 that is preferably constructed as an integral unit with the column; its operation is described hereinbelow with reference to FIG. 2. Typically, the column and its integral impeller are provided as a single-use, disposable assembly. The term "column" is used to describe a vertically oriented container, preferably cylindrical, having a longitudinal axis in which liquid is caused to flow upward and a length much greater than its diameter. The column 38 includes a bottom chamber 40 and an upper chamber or gas trap 42; it is connected to pole 26 by a bracket 39, which surrounds the bottom chamber portion of the column and holds it in the operative position that is shown in FIG. 1. Unlike the column, the pole and bracket are typically supplied as reusable components, which may be fixed to the dialysis machine as shown in FIG. 1.

Bracket 39 may contain a stator, as described hereinbelow, which magnetically drives the impeller to rotate the blood in column 38. Alternatively, shown in FIG. 1B is an embodiment of a device 20a that does not employ a rotatable impeller 46; instead the bracket may be formed to contain or to carry ultrasonic transducers 39a, for example of the type disclosed in FIG. 1 of U.S. Pat. No. 6,953,438, the disclosure of which is incorporated herein by reference, which transducers 39a direct ultrasonic energy radially into the column from multiple directions. The ultrasonic energy drives the bubbles toward the central axis of the column. As a result, microbubbles in the liquid are uniformly concentrated at the axial center of the vertical column and rise vertically upward so that they enter the flared entrance at the lower end of the tubular gas trap 42. The annular transducer may also be of the type shown and described in U.S. Pat. No. 6,953,438; it may be made in two halves interconnected by a hinge (or in three interconnected thirds) to facilitate its placement about the column at a location between the lower side inlet 44 and the upper side outlet 56.

Although the term "bubbles" is used throughout, the general concern is with the removal of microbubbles, which "bubbles" should be understood to include. In both magnetic and ultrasonic implementations, bracket 39 may form a closed circular clamp which fits around column 38, or it may be partly open to facilitate insertion and removal of the column. Integration of the magnetic driver or the ultrasonic transducers with the bracket simplifies the construction of the gas-bubble-removal device and enables easy, reliable installation and replacement of the disposable part of the device.

Figure 1C:
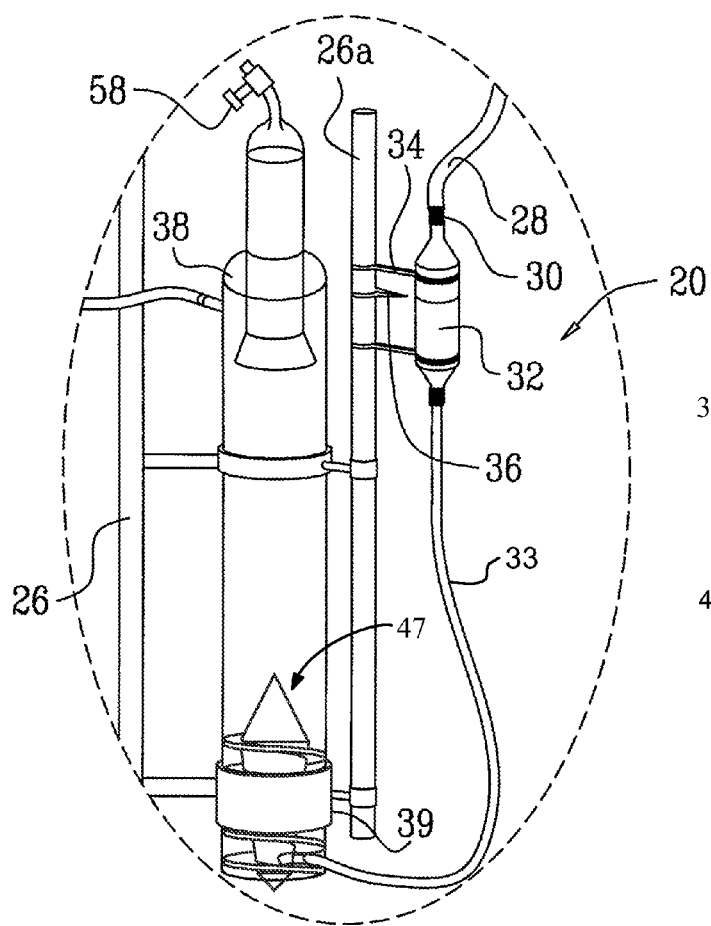
FIG. 1C is an enlarged fragmentary perspective view of the portion of an apparatus as generally shown in FIG. 1 depicting another alternative embodiment of the portion of the broken line encirclement.
Figure 1D:
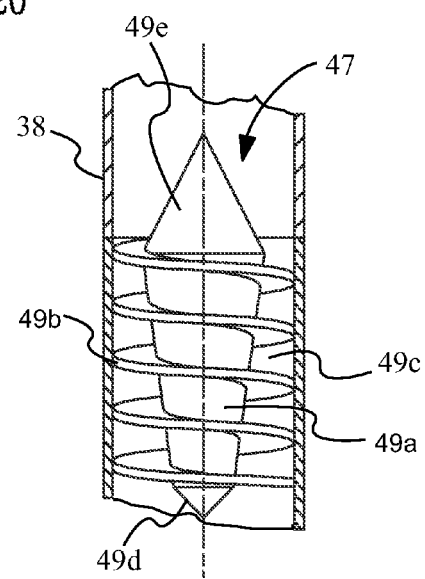
FIG. 1D is an enlarged fragmentary cross-sectional view of a portion of the apparatus shown in FIG. 1C.

In yet another embodiment which is depicted in FIGS. 1C and 1D, the impeller at the lower end of chamber 40 is replaced by a stationary cyclone-like device 47, which uses the pressure of the fluid itself to engender the rotation needed to focus the rising bubbles axially of the cylindrical chamber 40 where they will enter the trap 42. Such a device may have a shape similar to that shown in U.S. Pat. No. 6,827,862, for example.

A static device 47 is located within the chamber 40 coaxial to the chamber axis. The device has a central core 49a which carries a helical land or rib 49b. A helical passageway 49c is formed between adjacent loops of the land, the core, and the surrounding wall of the chamber 38, with which the edge of the land 49b is juxtaposed. Blood flows upward through the helical passageway 49c, which extends from its downstream inlet to its upstream exit at the end of the land. The gas-containing blood from the tubing 33 enters, substantially tangentially through an inlet, into the passageway 49c where it is forced to travel along a helical path. The blood then exits in an upward cyclonic eddy current.

The diameter of the core 49a is smallest at its upstream end and increases in the downstream direction, changing the root of the land and decreasing the volume of the passageway. In any event, the core 49a is preferably shaped so that the helical blood flow passageway has a flow cross section which becomes continuously smaller in the direction of flow so that the gas-containing blood is accelerated downstream and enters the cyclone eddy region above the device 47 at its greatest velocity.

At its upstream point, the core 49a preferably has a conical tip 49d directed opposite the flow of blood and at its downstream end, has a conical tip 49e directed in the direction of the flow. Instead of such conical tips, the core may have rounded end surfaces.

Thus, the gas-containing blood which enters tangentially into the passageway at its inlet flows helically through the static device 47 to its outlet end. This produces centrifugal forces which force the blood phase radially outward. As the blood phase is heavier than the gas, the gas is axially focused in the interior of cyclone eddy region above the device 47. The gas bubbles within this axially center region rise vertically upward and enter the coaxial gas trap 42.

Blood flows through the low pressure pump of the dialysis machine 22 to the gas removal device 20 via a tube 28 to an optional valve 30, which controls the rate of blood flow into a drip chamber 32 which is also optional; the drip chamber is connected by tubing 33 to an inlet near the lower end of the column 38. The drip chamber is mounted to an ancillary pole 26a by a suitable bracket 34. The connection of the drip chamber 32 to the ancillary pole in this manner by a vertically adjustable mounting permits the height of the drip chamber to be set so as to control the hydrostatic pressure head of liquid in column 38. The height of the drip chamber 32 relative to the column 38 is preferably varied during the course of the infusion procedure for one patient for the purpose as described hereinbelow. One or more gradations 36 may be provided on pole 26a as indicators of desired heights at which the nurse or other caregiver should align the drip chamber. Alternatively, when the drip chamber is omitted, the roller pump in the standard dialysis machine may be relied upon to force the blood through the separator. Other means, such as a hand-operated pump (as shown in FIG. 2), may instead be used to control the air pressure at the top of column 38.

FIG. 2 is a schematic view shown in cross-section, wherein the column is used in a different environment. In this embodiment, a finite amount of blood for infusion to the patient is supplied from a bag 41, rather than as a fairly continuous flow from a dialysis machine, but the principles of operation of the column 38 as a part of an overall bubble-separation device are unchanged. Blood from the bag 41 enters the drip chamber 32A via a valve 30 and flows through flexible tubing into a lower region of the bottom chamber 40 of column 38 through a side inlet 44. Alternating or other current passed through a stator 48 (which is typically contained in a mounting bracket 39, as noted above) causes impeller 46 to rotate. The resulting rotational movement of blood 52 in the bottom chamber 40 drives the heavier blood radially outward causing bubbles 54 in the blood to concentrate and rise along the central flow axis of the column where they enter into a bubble trap 42 which forms the upper end thereof through a flared lower entrance thereto. Chamber 40 and trap 42 are typically formed upon an inert, transparent material, such as a suitable glass or polymeric material; in a cylindrical shape, although materials of other types and shapes may also be used. Following removal of the bubbles in this manner, the blood flows out through an outlet 56 where it is directed downward through tubing to a patient.

The rotation of impeller 46 is induced due to one or more permanent magnets that are appropriately arranged in the impeller. The external body of the impeller is typically molded from a biocompatible plastic or fashioned from a non-magnetic metal. In the embodiment shown in FIG. 2, the impeller floats freely within the column by magnetic levitation, so that no bearings are needed. This sort of blood pump, known as a "maglev" system, is described, for example, by Hoshi et al., in "Third-generation Blood Pumps with Mechanical Noncontact Magnetic Bearings," *Artificial Organs* 30(5), pages 324-338 (2006), which is incorporated herein by reference. The body of the impeller is preferably ovoid having a plurality of curved blades which create the radially outward and slightly upward flow of blood upon rotation of the impeller. The impeller, in various configurations, can be also without blades and use drag forces to force the fluids to rotate. The impeller would normally rest on the flat bottom of the column until the magnetic drive is energized, when it would be raised and centered through magnetic force and caused to rotate within the liquid at the bottom of the lower chamber 40 of the bottom chamber of the column.

Figure 3A:
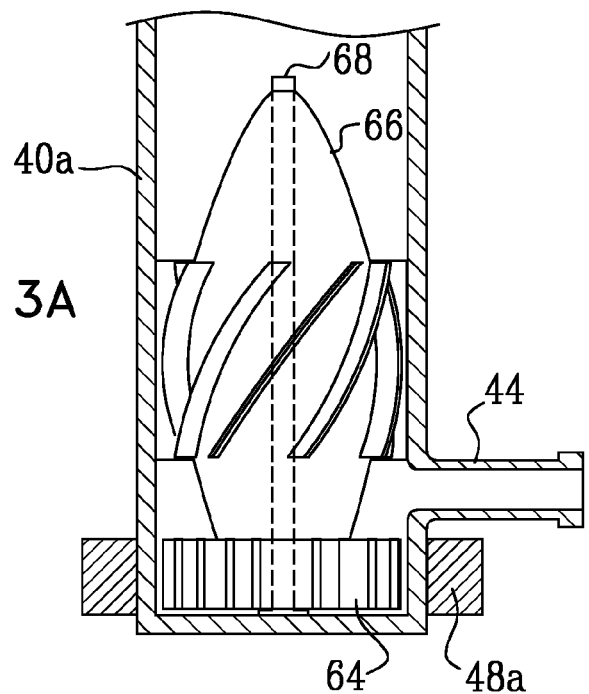
FIG. 3A is a schematic cross-sectional fragmentary view showing details of an alternative embodiment an impeller that may be used in a column like that shown in FIG. 1.
Figure 3B:
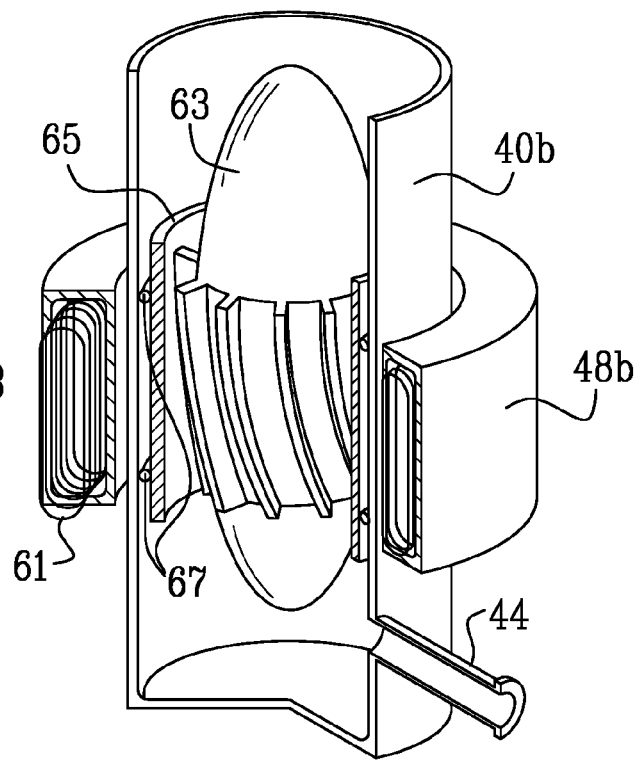
FIG. 3B is a schematic cutaway view showing details of another alternative embodiment of an impeller that may be used in a column like that shown in FIG. 1.

Although this preferred free-floating impeller/column arrangement has particular advantages, other types of impellers may alternatively be used. Two such alternatives are shown in FIGS. 3A and 3B and described hereinafter. In addition, instead of using an impeller to cause the centrifugal flow of blood in an outward radial direction as it rises in the column, a plurality of ultrasonic transducers disposed in an annulus positioned around a column, vertically above the lower liquid inlet, as shown in FIG. 1B, can be used to effectively cause whatever gas bubbles are present to move to a central location along the axis of the column as described briefly hereinafter. are present to move to a central location along the axis of the column as described hereinafter with respect to FIG. 4.

To facilitate removal of bubbles 54, without requiring continuous active venting of the gas accumulated in the trap 42, a vacuum is created at an upper end 60 of column 38 in the gas trap chamber 42, the entrance to which is just below the vertical level of the side outlet 56. The term "vacuum" is used in the context of the present patent application to include partial vacuums, in which the pressure is significantly lower than the ambient atmospheric pressure. The vacuum increases the tendency of the bubbles 54 to move upward in the column of liquid in the gas trap 42 until they reach the upper surface where the bubbles burst.

Vacuum may be created in FIGS. 1 and 2 using drip chamber 32 as a pressure control device; the pressure in column 38 is controlled by changing the height of the drip chamber that is supplying the liquid. Initially, before permitting blood to flow into the patient's vein, the drip chamber 32, 32A is elevated to the position where the liquid level in it will be at the level marked A in FIG. 2, for example. With the drip chamber in this position, the blood level in the drip chamber will be near the upper end 60 of the gas trap 42. A valve 58 attached to tubing at the top of the gas trap is opened, and blood is allowed to flow into column 38, with the side outlet 56 closed, until the blood level in the column reaches the level A near the upper end. This valve 58 is then closed, and the drip chamber 32, 32A is then lowered, typically to the position marked B just above the side outlet 56. The resulting reduction of liquid pressure head in column 38 that results causes a vacuum to form at upper end 60 of the gas trap chamber 42 which supports a column of liquid therein to a level between A and B. Thus, by this simple mechanical operation, the desired vacuum is created without any need for an external vacuum pump or other suction connection.

The drip chambers 32 and 32A are examples of liquid level-setting devices that may serve as the pressure control device. Alternatively, the height of a liquid container, such as bag 41 itself or a conduit carrying liquid to column 38, may be manipulated in order to effect such a desired change of pressure head in the column.

Optionally, a hand-operated balloon pump 59 may be connected to the valve 58 at upper end 60 of the column 38. If the foregoing sequence was used and air could not escape to relieve pressure build-up in upper end 60, pump 59 is compressed while valve 58 remains closed; and then valve 58 is opened while pump 59 is released in order to draw accumulated gas from upper end 60 into the pump. Valve 58 may simply comprise a one-way valve, with a second one-way valve at the exit from pump 59; in such case, the above procedure may be carried out without actively opening or closing valve 58. Alternatively, if the arrangement as illustrated in FIG. 2 is used, it may not be necessary to move the location of the drip chamber 32A. If desired, it may be originally set at so that liquid level is at level B. Then, once the liquid level within the column 38 reaches that level, a slow actuation of the hand-operated balloon pump 59 can be used to create a vacuum in the upper end of the gas trap which will cause the liquid column to rise in the gas trap 42 to a desired level, indicative of the desired amount of vacuum to assist in promoting subsequent gas removal from the liquid that is being gravity fed upward through the column 38.

FIG. 3A is a schematic, sectional view showing details of an alternative embodiment of an impeller 66 that may be used in such a chamber 40a of a bubble-separation column. In this embodiment, the impeller 66 is mounted on a shaft 68 and rides on a magnetic rotor 64. The rotor rotates under the influence of the AC magnetic field supplied by stator 48a. (In this case, as can be seen in FIG. 3A, the supporting bracket that conveniently contains the stator 48a would be positioned around the bottom of chamber 40a, rather than higher up as in the FIGS. 1 and 2 embodiments.) The configuration of FIG. 3A may be advantageous in permitting the use of a closed bracket in which the chamber 40a may be set, with a closed annular stator surrounding the chamber 40a, rather than an open stator 48 as may be required to facilitate its interconnection with column 38 in the FIGS. 1 and 2 embodiments.

FIG. 3B is a schematic, cutaway view showing details of another impeller 63 that may be used in a similar chamber 40b, in accordance with yet another embodiment of the invention. A stator coil 61 is carried inside the body of a hollow bracket/stator 48b. Impeller 63 is axially affixed within a magnetized sleeve 65, having north and south poles at diametrically opposite regions. The AC magnetic field generated by stator coil 61 causes sleeve 65 to rotate within chamber 40b and thus turn impeller 63. The outer diameter of the magnetized sleeve is slightly less than the inner diameter of chamber 40, and bearings 67 are preferably interposed between the outer surface of sleeve 65 and the inner surface of chamber 40b to enhance the stability of the impeller and reduce friction.

As particularly evident from the FIGS. 1B and 1C embodiments, the upward flow through the chambers 30 is caused by gravity, driven by the pressure head of liquid, e.g. blood, and not caused by the relatively slow rotation of any impeller, which may turn at, e.g. 1 to 10 rpms, or even 1 to 2 rpms. Alternatively, as mentioned hereinbefore, the flow could be the direct result of a roller pump in the dialysis machine.

Although the embodiments described hereinabove refer mainly to removal of gas bubbles from blood, the principles may similarly be applied in removing gas from liquids of other sorts before they are infused. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description. For example, if the FIG. 1B embodiment were employed, a drive circuit (not shown) would provide electrical energy to drive the annular transducer. Optionally, a bubble sensor may be used to detect concentrations of bubbles in the blood entering the column. Such sensor may comprise, for example, a Doppler ultrasound sensor, which detects the bubbles by their movement. The drive circuit may then intermittently actuate the annular transducer in response to the signals from sensor, so that the transducer operates only when a significant concentration of bubbles is entering the device. This sort of intermittent operation may be advantageous in reducing power consumption and potential undesirable heating both of the blood and the transducer.

The invention claimed is:

1. Apparatus for removing bubbles from a liquid to be infused to a patient, the apparatus comprising:
a feed liquid container;
means for supplying blood to said feed liquid container;
a vertical column, having a lower end and an upper end, and having an inlet adjacent the lower end for receiving liquid from said feed liquid container, a side outlet vertically thereabove for exit of the liquid from the column, and a gas trap adjacent the upper end;
a bubble-separator which causes bubbles in the liquid entering the column to move toward a central axis of the column as the liquid travels from the inlet to the outlet so that the bubbles enter the gas trap; and
means for creating a vacuum in an upper region of the gas trap, which means comprises means for supporting the feed liquid container at different vertical locations so as to control the pressure head in the column and create a vacuum in an upper region of the gas trap.

2. The apparatus according to claim 1, wherein said feed liquid container comprises a drip chamber.

3. The apparatus according to claim 2, wherein the supporting means comprise a pole having gradations indicating respective heights at which to position and then reposition the feed liquid container so as to create the desired vacuum in the gas trap.

4. The apparatus according to claim 3, wherein the respective heights comprise a first height at about the upper end of the column and a second lower height that is near but vertically above the side outlet from the column, wherein the vacuum is created when the feed liquid container is repositioned to the second height after the column is filled with liquid to a level above said side outlet.

5. The apparatus according to claim 1 wherein said column has a length greater than its diameter and wherein said gas trap is located in an axial central region thereof and has an entrance vertically below the side outlet.

6. The apparatus according to claim 1, wherein said bubble-separator comprises a magnetic rotor contained within the column, and wherein a stator, exterior of the column, is configured to generate a magnetic field so as to cause the rotor to rotate.

7. The apparatus according to claim 6, wherein the rotor and stator are configured so that the rotor is held in place by magnetic levitation while rotating within the column.

8. The apparatus according to claim 6, wherein the column has a cylindrical inner surface, and wherein the rotor comprises a magnetic sleeve, which rotates on bearings against the inner surface of the column.

9. The apparatus according to claim 1, wherein the bubble-separator comprises a plurality of ultrasonic transducers, which are configured to direct ultrasonic energy radially inward toward the axis at a location vertically between said inlet and said outlet.

10. A method for removing bubbles from a liquid prior to infusion into a patient, which method comprises:
supplying the liquid which contains bubbles to a drip chamber,
supplying said liquid from the drip chamber by gravity flow so as to (1) enter a vertically oriented column through an inlet adjacent to a lower end thereof, which vertical column has a length greater than its diameter and a gas trap located along its central axis and adjacent to its upper end, and (2) exit from the column via a side outlet located vertically higher than the inlet;
positioning the column at a location vertically higher than the patient and maintaining the vertical column in an operative position during flow of said liquid through the column;
providing a bubble-separator which is located between the inlet to the column and the side exit which directs said liquid and bubbles flowing upward in the column so as to cause bubbles to move toward the central axis where they rise and enter the gas trap as said liquid moves radially outward and exits from the side outlet,
directing said exiting liquid, with gas bubbles removed, from the side outlet to a lower location to effect gravity flow of liquid through the column, and
creating a vacuum in the gas trap by moving the drip chamber vertically relative to the column to change the pressure head being applied to the column by said liquid flowing into the column.

11. The method according to claim 10, wherein said liquid is blood being supplied by a dialysis machine pump to the drip chamber.

12. The method according to claim 11, wherein the bubble-separator comprises a stator exterior of the column and a magnetic rotor within the column, and a magnetic field is generated in the stator so as to cause the rotor contained within the column to rotate.

13. The method according to claim 12, wherein the rotor and stator are configured so that the rotor is held in place by magnetic levitation while rotating within the column.

14. The method according to claim 11, wherein the bubble-separator comprises ultrasonic transducers, and wherein the ultrasonic transducers are driven to direct ultrasonic energy radially toward the axis of the column.

* * * * *